United States Patent [19]

Goodrich et al.

[11] Patent Number: 5,178,884

[45] Date of Patent: Jan. 12, 1993

[54] LYOPHILIZED AND RECONSTITUTED RED BLOOD CELL COMPOSITIONS

[75] Inventors: Raymond P. Goodrich; Christine M. Williams; Roger W. Hackett, all of Pasadena, Calif.

[73] Assignee: Cryopharm Corporation, Pasadena, Calif.

[21] Appl. No.: 374,171

[22] Filed: Jun. 29, 1989

Related U.S. Application Data

[63] Continuation-in-part of Ser. No. 360,386, Jun. 2, 1989, Pat. No. 5,043,261, which is a continuation of Ser. No. 335,557, Apr. 10, 1989, abandoned, which is a continuation-in-part of Ser. No. 195,745, May 18, 1988, which is a continuation-in-part of Ser. No. 237,583, Aug. 25, 1988, abandoned.

[51] Int. Cl.$^5$ .............................................. A61K 35/18
[52] U.S. Cl. ..................................... 424/533; 424/529; 424/450; 435/2; 514/6
[58] Field of Search .................... 435/2; 424/529, 533; 514/6

[56] References Cited

U.S. PATENT DOCUMENTS 3,344,617 10/1967 Rinfret et al. .
3,347,745 10/1967 Rinfret et al. .
4,572,899 2/1986 Walker et al. .
4,806,343 2/1989 Carpenter et al. ................ 514/6
4,874,690 10/1989 Goodrich, Jr. et al. .

FOREIGN PATENT DOCUMENTS 342879 11/1989 European Pat. Off. .
356257 2/1990 European Pat. Off. .
3007913 9/1981 Fed. Rep. of Germany .
8606585 11/1986 PCT Int'l Appl. .

OTHER PUBLICATIONS

Scheiwe et al., Cryobiology vol. 19, No. 5, (1982) pp. 461–477.
Green Cross Corp.—Chem. Abst. vol. 99 (1983) p. 156, 728y.
Scheiwe et al.—Chem. Abst. vol. 98 (1983) p. 14029b.

*Primary Examiner*—Sam Rosen
*Attorney, Agent, or Firm*—Heller, Ehrman, White & McAuliffe

[57] ABSTRACT

A process and medium are disclosed for the lyophilization of red blood cells which comprises the use of solutions including monosaccharide hexoses and pentoses, and biocompatible amphipathic polymers to permit the reconstitution of viable red blood cells. Also disclosed are lyophilized and reconstituted erythrocyte and hemosome containing compositions.

21 Claims, 4 Drawing Sheets

LYOPHILIZED AND RECONSTITUTED RED BLOOD CELL COMPOSITIONS

This application is a continuation-in-part of copending commonly assigned Ser. No. 360,386, filed Jun. 2, 1989 now U.S. Pat. No. 5,063,261; which is a continuation of copending commonly assigned Ser. No. 335,557, filed Apr. 10, 1989 now abandoned; which is a continuation-in-part of Ser. Nos. 195,745, filed May 18, 1988, and 237,583, filed Aug. 25, 1988 now abandoned, the disclosures of which are incorporated herein by reference in their entirety.

FIELD OF THE INVENTION

This invention relates to the general field of biochemistry and medical sciences, and specifically to novel lyophilized and reconstituted red blood cell compositions.

BACKGROUND OF THE INVENTION

Blood is a major tissue of the human body, and has as a predominant role the delivery of oxygen from the lungs to peripheral tissues. This role is carried out by erythrocytes, i.e., red blood cells (RBC). The oxygen is furnished to the peripheral cells from the lungs by an exchange-diffusion system brought about by a red, iron-containing protein called hemoglobin. When hemoglobin combines with oxygen, oxyhemoglobin is formed and when oxygen is given up to the tissues, the oxyhemoglobin is reduced to deoxyhemoglobin.

The red cell membrane is composed of two major structural units, the membrane bilayer and a cytoskeleton. A lipid bilayer and integral membrane proteins form the membrane bilayer, which has little structural strength and fragments readily by vesiculation. The other major component, the membrane skeleton, stabilizes the membrane bilayer and provides resistance to deformation. The cytoskeleton is linked to the bilayer in the erythrocyte membrane, possibly by lipid-protein as well as protein-protein associations. The hemoglobin, and other RBC components, are contained within the red cell membrane.

In adults, bone marrow is active in the formation of new red blood cells. Once erythrocytes enter the blood, these cells have an average lifetime of about 120 days. In an average person, about 0.83% of the erythrocytes are destroyed each day by phagocytosis, hemolysis or mechanical damage in the body, and the depleted cells are renewed from the bone marrow.

A wide variety of injuries and medical procedures require the transfusion of whole blood or a variety of blood components. Every patient does not require whole blood and, in fact, the presence of all of the blood components can cause medical problems. Separate blood fractions can be stored under those special conditions best suited to assure their biological activity at the time of transfusion. For example, when donor blood is received at a processing center erythrocytes are separated and stored by various methods. Such cells are storable in citrate-phosphate-dextrose at 4° C. for up to five weeks, generally as a unit of packed erythrocytes having a volume of from 200 to 300 ml and a hematocrit value (expressed as corpuscular volume percent) of 70 to 90. Erythrocytes may also be treated with glycerol and then frozen at from $-30°$ to $-196°$ C. and stored for up to seven years in a glycerol solution, but must be kept frozen at low temperatures in order to survive sufficiently for transfusion. Both these methods require careful maintenance of storage temperature to avoid disruption of the desired biological activity of the erythrocytes, and provide a twenty-four hour survival time for at least 70% of the transfused cells, which is considered to be an acceptable level for use in transfusion practice in accordance with the American Association of Blood Bank standards.

It has thus been a desideratum to obtain reconstitutable red blood cells which can be stored at high storage temperatures (4° C. to room temperatures) with good shelf life. Such red blood cell compositions would facilitate the availability of erythrocytes for medical purposes.

Prior to the present invention, it has been believed to be impossible to freeze-dry erythrocytes in a manner which permits the reconstitution of the cells to form erythrocytes with an intact cytoskeleton and biologically-active hemoglobin, i.e., viable red blood cells. Viable RBC's can be characterized by one or more of the following: capability of synthesizing ATP; cell morphology; $P_{50}$ values; oxy, met and heme values; MCV, MCH, and MCHC values; cell enzyme activity; and in vivo survival. When RBC's have been lyophilized according to previous methods, for example in either an aqueous or phosphate-buffered saline (PBS) solution, the reconstituted cells are damaged to the extent that the cells are not capable of metabolizing or synthesizing ATP, and the cell hemoglobin cannot transport oxygen. Glutaraldehyde-fixed erythrocytes, which have been lyophilized and reconstituted, have found use primarily in agglutination assays.

SUMMARY OF THE INVENTION

The compositions provided by the present invention allow for storage under normal conditions, while maintaining the structure of the cell and the biological activity of the hemoglobin. The compositions of the present invention may be reconstituted and used on a therapeutic level. Briefly, the compositions are made by immersing a plurality of erythrocytes, and/or hemosomes, in a physiologic buffered aqueous solution containing a carbohydrate, and a biologically compatible polymer, preferably having amphipathic properties. By the term amphipathic it is meant there are hydrophobic and hydrophilic portions on a single molecule. This immersion is followed by freezing the solution, and drying the frozen solution to yield novel freeze-dried erythrocytes containing less than 10%, and preferably about 3% or less by weight of moisture, which, when reconstituted, produce a significant percentage of viable, transfusably useful red blood cells, or hemosomes. Methods of reconstitution of the red blood cells or hemosomes are also provided.

DETAILED DESCRIPTION OF THE INVENTION

Figure 1:
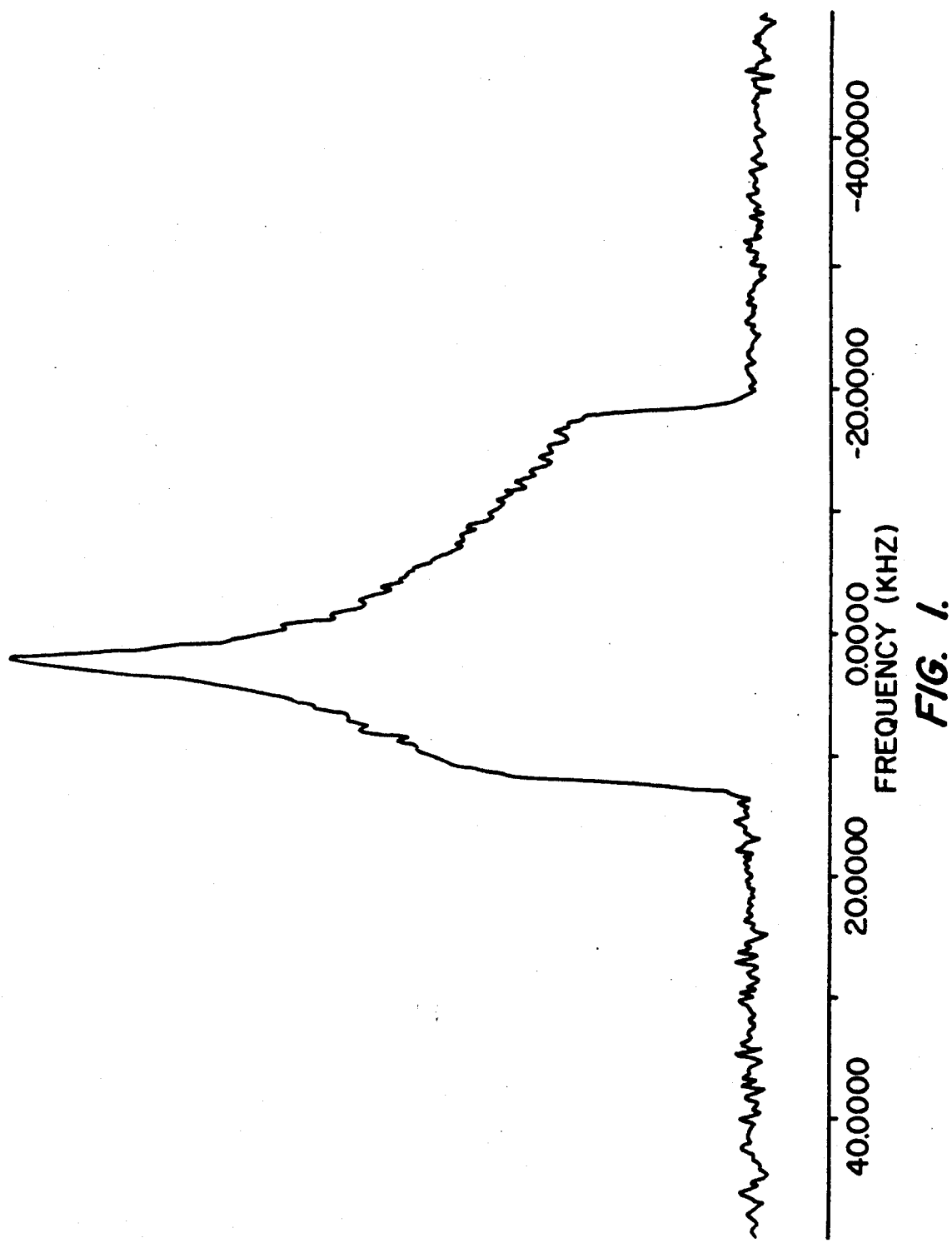
FIG. 1 is a phosphorous-31 NMR spectrum at 162 MHz of solid barium diethylphosphate.

The carbohydrate utilized to prepare erythrocyte and/or hemosome compositions according to the invention is biologically compatible with the erythrocytes or hemosomes, that is, non-disruptive to the cells or hemosome membrane, and one which permeates, or is capable of permeating, the membrane of the erythrocytes or hemosomes. The carbohydrate may be selected from the group consisting of monosaccharides, since disaccharides do not appear to permeate the membrane to any significant extent. Monosaccharide pentoses and hexoses are preferred as is a final concentration of from about 7.0 to 37.5 weight % in phosphate buffered saline (PBS), preferably about 26%. Xylose, glucose, ribose, mannose and fructose are employed to particular advantage.

The invention will be hereafter described in connection with erythrocytes (RBC's) but it will be understood it is also applicable to hemosomes.

The polymer may be present in the solution in concentrations of from a final concentration of about 1 K weight % up to saturation, and has a molecular weight in the range of from about 5 K to about 360 K. Preferably, the polymer has a molecular weight in the range of from about 2.5 K to about 80 K, most preferably from about 5 K to 50 K, and is present in a concentration of from about 3.6 weight % up to the limit of solubility of the polymer in the solution. Polymers selected from the group consisting of polyvinylpyrrolidone (PVP) and polyvinylpyrrolidone derivatives, and dextran and dextran derivatives provide significant advantages. Most preferred is the use of polyvinylpyrrolidone (an amphipathic polymer) of average molecular weight of in the range of 10-40 K in an amount in the range of 12-20% weight by volume in the solution prior to lyophilization. Amino acid based polymers (i.e., proteins), dextrans or hydroxyethyl starch may also be employed. Other amphipathic polymers may be used, such as poloxamers in any of their various forms. The use of the carbohydrate-polymer solution in the lyophilization of red blood cells allows for the recovery of intact cells, a significant percentage of which contain biologically-active hemoglobin. While not intending to be bound by any theory, the amphipathic properties of the polymer allow them to bind to the cell membrane while protecting the membrane surface by extension of the hydrophilic portion into the aqueous environment. This may alleviate the damage to the cell membrane which causes other problems, such as cell aggregation.

A polyanion may be used in the washing of the reconstituted RBC's. It may be any polyanion which is non-disruptive to the cell membrane of the erythrocytes, and polyanions having multiple phosphate, sulfate or carboxylate groups are preferred and may be present in amounts of from 0.01 weight percent up to saturation in the solution although final concentrations in the range of from about 0.1 weight % up to about 10 weight % is advantageous. More preferably, the polyanion is a compound having multiple anionic groups which are phosphate, sulfate or carboxylate groups. Specifically, polyanions selected from the group consisting of pyrophosphate, tripolyphosphate, phosphorylated inositols (including triphosphoinositide and inositol hexaphosphate), 2,3-diphosphoglycerate, adenosine triphosphate, and heparin may be employed to significant advantage.

The most preferred inositol hexaphosphate concentration range is 20-90 mM.

As is shown by the data set forth below, the described solutions provide media which permit red blood cells to be subjected to the stresses of freezing, sublimation and reconstitution and to form freeze-dried red blood cells which may be reconstituted to yield cells which are capable of functioning as erythrocytes in mammals.

All percentages set forth herein are expressed as weight percentages indicating weight of the solute versus the total weight of the solution unless otherwise indicated, and weight/volume percentages indicate weight of solute versus total volume of the solution.

As noted above, the process of the invention provides a medium for the lyophilization and reconstitution of intact and biologically-active erythrocytes. While the media of the invention are novel it will be understood that apparatus and related techniques are known by those of skill in the art for the lyophilization of various materials, and cells in particular, and only the specific temperatures and apparatus employed in the examples are described herein. From this description, one of ordinary skill in the art will be capable of employing the media of the invention in a process for the freeze-drying and reconstitution of intact, viable red blood cells.

The term lyophilization is broadly defined as freezing a substance and then reducing the concentration of one of the solutes, namely water, by sublimation and desorption, to levels which will no longer support biological or chemical reactions. Usually, the drying step is accomplished in a high vacuum. However, with respect to the storage of cells and particularly erythrocytes, the extent of drying (the amount of residual moisture) is of critical importance in the ability of cells to withstand long-term storage at room temperature. In the method of the invention, cells may be lyophilized to a residual water content of less than 10 weight %, preferably less than 3%, and still be reconstituted to transfusable, therapeutically useful cells. Cells with about 3 weight % water content made in accordance with the present invention have been stored for up to two weeks at room temperature, and at 4° C. for longer than eight months, without decomposition. This far exceeds the current A.A.B.B. standard for frozen or refrigerated cells of six weeks at 4° C. or less than one day at room temperature without decomposition.

The lyophilization solution will be buffered in the range of pH of 7.0 to 7.4 preferably by a phosphate-buffered saline solution. A typical phosphate-buffered saline solution will comprise mono- and di-basic sodium phosphate (usually around 10 mM), sodium chloride (usually about 150 mM) and 10 mM adenosine. This solution maintains the pH at around 7.2.

A preferred phosphate-buffered saline solution to be used as the lyophilization buffer will comprise pyruvate, inosine, adenine, potassium chloride, sodium chloride, and dipotassium phosphate, all of which will serve as a basic salt buffer at a pH of about 7.2. In addition this lyophilization buffer will contain a final concentration of about 30% weight by volume of a monosaccharide, preferably 26% (1.44 M) glucose, and a final concentration of about 16% weight by volume of polyvinylpyrrolidone (average molecular weight of 40 K).

Another feature of the invention is that the lyophilization buffer serves as a cryoprotectant. The blood cells dried with this protectant exhibit a phosphorous-31 NMR spectrum with a lineshape pattern characteristic of a membrane structure associated in a bilayer in a gel phase, and indicates that some membrane mobility is retained as shown by stereochemical alteration in the phospholipid headgroups. On the other hand, cells dried without the protectant show a lineshape pattern indicating loss of membrane bilayer structure, evidence of headgroup rigidity, and possible formation of hexagonal phase lipid structure which is incompatible with cell viability. Additionally, the phosphorous-31 NMR linewidth for cells dried with the protectant is reduced by at least 8% compared to the linewidth for similar cells dried without the protectant. This reduction in phosphorous-31 NMR linewidth may vary, depending upon the particular sample, from 8% to about 20%.

The erythrocytes will preferably be prepared from whole blood centrifugation, removal of the plasma supernatant and resuspending the pellets in PBS. This wash cycle may be repeated 2–3 times, then the packed cells are diluted with the lyophilization buffer described above so that the final diluted concentration of carbohydrate and polymer are maintained in the necessary ranges.

Alternatively, commercially available packed blood cells may be used, which typically are prepared in CPDA (commercial solution containing citrate, phosphate, dextrose and adenine).

Upon lyophilization by conventional techniques to a moisture content of less than 10%, and preferably less than 3%, the lyophilized cells may be maintained under vacuum in vacuum-tight containers, or under nitrogen or other inert gas, at room temperatures for extended periods of time in absence of or without significant degradation of their desirable properties when reconstituted for use as transfusable cells. It is a particular advantage of the present invention that the lyophilized cells may be stored at room temperature for extended periods of time, thus obviating the need for low temperature refrigeration which is required for storing lyophilized red blood cells prepared by methods of the prior art.

It is a further advantage of the present invention that the lyophilized red blood cells may be reconstituted at normal temperatures, i.e. greater than about 17° C. up to about 37° C., which corresponds to normal human body temperature, and preferably at room temperature (about 22° C.). The reconstitution medium is preferably a solution comprising a polymer or mixture of polymers having a molecular weight of from about 2.5 K to 360 K, preferably 5 K to about 360 K, present in a concentration in the range of about 12 to 30% weight by volume. This polymer may be the same polymer utilized to lyophilize the red blood cells as described above. Hence the polymers polyvinylpyrrolidone, hydroxyethyl starch, and dextran are particularly preferred and most preferred is polyvinylpyrrolidone present in a concentration of about 19% weight by volume in the reconstitution solution. The reconstitution solution will be buffered again typically by phosphate-buffered saline as described hereinabove to maintain a pH within the range of about 7.0 to 7.4. The most particularly preferred polymer is polyvinylpyrrolidone of an average molecular weight of about 10 K.

The most preferred reconstitution buffer will be a solution comprising pyruvate, inosine, adenine, potassium chloride, sodium chloride and dipotassium phosphate, all of which form a basic salt buffer at a pH of about 7.2, which also contains about 19% weight by volume of polyvinylpyrrolidone (average molecular weight about 10 K).

The reconstitution solution may also optionally contain a monosaccharide, preferably present in the concentration range of about 7.0 to 37.5% weight by volume. The preferred monosaccharides are xylose, glucose, ribose, mannose and fructose.

In the most preferred embodiment, the lyophilized erythrocytes can be reconstituted by mixing with an equal volume of the reconstitution buffer at a temperature of about 37° C. and mixed until fully hydrated. By "equal" it is meant that the volume is the same as the starting volume prior to lyophilization.

Then, it is preferred that the rehydrated erythrocytes be washed according to the following procedure. It is realized, however, that once the erythrocytes are reconstituted with reconstitution buffer they are in a transfusably-useful form, but the combination of washings described hereinafter are preferred, specifically for use of the cells for clinical purposes.

After separating the erythrocytes from the reconstitution buffer by centrifugation, the resulting erythrocytes, usually in the form of a pellet, are preferably resuspended in (approximately the volume used in the reconstitution) a washing buffer comprising the basic salt buffer at pH 7.2, described above, further containing about 16% weight by volume polyvinylpyrrolidone (molecular weight about 40 K). Separation by centrifugation completes the first post-rehydration step, a washing step.

For the second step, the washed cells are resuspended in the washing buffer and a glycolytic intermediary solution (GIS) is added. The total volume is preferably ten times the volume of packed cells present. The volume of washing buffer should be sufficient to effect a ten-fold dilution of the volume of added GIS. The GIS will contain the following:
ADP
NAD
adenine
adenosine
inosine
$Na_2HPO_4$
$CaCl_2$
$MgCl_2.6H_2O$ The cells in this suspension are then incubated, preferably at room temperature, for about 30–60 minutes. It will be realized that the duration and temperature of the incubation may vary from these conditions as long as it is not detrimental to the cells. While not intending to be bound by a theory, it is believed that the incubation restores cofactors important for ATP synthesis to the cells lost during lyophilization.

After a sufficient period of incubation, the suspension is centrifuged to complete the second post-hydration step.

The third post-rehydration step is an iso-osmotic pulsing step in which the erythrocytes are resuspended in an iso-osmotic solution comprising inositol hexaphosphate (IHP) (at a final concentration of about 0.1 to 7% wt/vol) preferably 20–90 mM, and polyethylene glycol (average molecular weight from 1 KD to 5 KD, preferably about 3.3 KD), at a pH of about 7.2. Other polyanions may be used in place of or in combination with IHP, such as, adenosine triphosphate, pyrophosphate or tripolyphosphate. This solution has an osmotic pressure of about 311 mOs. After approximately a 10–50 fold dilution, by adding washing buffer so that the approximate volume is that used in the reconstitution, the suspension is centrifuged to complete the third post-hydration step.

For the fourth post-hydration step the packed erythrocytes are incubated for about 30 minutes at about 37° C. before being resuspended in a phosphate-buffered-glucose-adenosine solution (PBS-GA), preferably containing about 5 mM glucose, and about 10 mM adenosine. This step is conducted at about 37° C. Centrifugation completes the fourth step. The wash is then repeated using the PBS-GA solution at room temperature as a fifth post-hydration step. After separation by centrifugation, this final step is completed.

The reconstituted cells according to the present invention have characteristics which render them transfusable and useful for therapeutic purposes in that their properties are similar to that of normal (i.e. not previously lyophilized) red blood cells. Typically reconstituted red blood cells according to the present invention have an oxyhemoglobin content greater than about 90% of that in normal red blood cells. Hemoglobin recovery prior to any washing step is typically in the range of 80 to 85%. The overall hemoglobin recovery including the post-hydration washing steps is about 20 to 30%. The morphology of the reconstituted cells according to the present invention (by scanning electron microscope) typically shows no holes or gaps, and discocytic or stomatocytic morphology. The oxygen carrying capacity of normal red blood cells (as measured by $P_{50}$, the pressure at which 50% of the oxygen molecules are bound) was measured to be in the range of about 26 to 28 (average 26.7); with an average Hill coefficient of 1.95. The typical $P_{50}$ for erythrocytes lyophilized and reconstituted according to the present invention is about 27.5 (average) with an average Hill coefficient of 2.08. Assays of ATP in the reconstituted cells indicate ATP levels suggesting normal ATP to ADP metabolism. Normal agglutination of red blood cells made according to the present invention is also typically found.

Having described the preferred embodiments of the present invention, the following examples are provided by way of illustration but are not intended to limit the invention in any way.

EXAMPLE 1

Red blood cells are centrifuged for 10 minutes at 1,500 RCF in a Mistral 3000 centrifuge. Plasma and buffy coat are removed. The cells are subsequently washed 2-3 times with PBS-GA (Dulbecco PBS, 5 mM glucose (0.90 g/l), and 10 mM adenosine (2.67 g/l)).

The cells are mixed in a freezing flask with lyophilization buffer, that was pre-warmed to 37° C., at a hematocrit of 10% and incubated for 30 minutes at 37° C. Cells and buffer are mixed immediately to prevent aggregation of cells.

The lyophilization buffer is as follows:

| | | |
|---|---|---|
| 10 mM pyruvate | 1.100 g/l | |
| 10 mM inosine | 2.682 g/l | |
| 5 mM adenine | 0.676 g/l | = basic salt |
| 75 mM NaCl | 4.380 g/l | buffer |
| 10 mM Na$_2$HPO$_4$ | 1.420 g/l | [pH 7.2] |
| + | | |
| 1.6M Glucose | 288.3 g/l | |
| 16% w/v Plasdone C-30 | 160 g/l | (polyvinyl pyrrolidone, 40 KD) |

The freezing flask is then rotated in liquid nitrogen to form an even shell, or, alternatively, placed on a flask freezer at −85° C. (MeOH) and rotated to form a shell and placed in liquid nitrogen. The samples are then transferred to a Labconco benchtop freeze-dryer. The samples are allowed to dry overnight, or until the sample is thoroughly dried to about 3% by weight moisture content (3.38%±0.13 (gravimetric); 2.388±0.2810 (Karl-Fischer)). To reconstitute the dried samples, an equal volume of pre-warmed reconstitution buffer is added in a water bath at 37° C. The sample is swirled until fully hydrated.

The reconstitution buffer is as follows:

| |
|---|
| basic salt buffer [pH 7.2] |
| + |
| 19% w/v Plasdone C-15 190 g/l |
| (polyvinylpyrrolidone, 10 KD) |

The reconstituted cells are centrifuged in the Mistral 3000 centrifuge at 1700 rcf for 10 min. (temperature setting: 20° C.).

The pellet is resuspended in washing buffer and centrifuged under the same conditions.

The washing buffer is as follows:

| |
|---|
| basic salt buffer [pH 7.2] |
| + |
| 16% (w/v) Plasdone C-30 160 g/l |
| (polyvinylpyrrolidone, 40 KD) |

The cells are resuspended in the wash buffer and the GIS buffer was added. Sufficient wash buffer is used to dilute the GIS buffer by about ten-fold. The GIS buffer is as follows:

| | mM | mg/100 ml |
|---|---|---|
| ADP | 1.38 | 67.2 |
| NAD | 50.0 | 331.7 |
| adenine | 50.0 | 67.6 |
| adenosine | 50.0 | 133.6 |
| inosine | 50.0 | 134.1 |
| Na$_2$HPO$_4$ | 10.0 | 142.0 |
| CaCl$_2$ | 5.0 | 73.5 |
| MgCl$_2$ · 6H$_2$O | 5.0 | 101.7 |

The suspension is incubated for 30–60 minutes, then centrifuged at 1700 RCF for 10 minutes.

The pellet is then resuspended in an IHP-solution (311 mOs) at a 10–50 fold dilution, and centrifuged at 500 RCF for 10 minutes.

The IHP solution is as follows:

| | |
|---|---|
| IHP dodecasodium salt (pH 7.2) | 33.3 g/l |
| (hexacalcium salt may be used or pure acid form of IHP) | (27 mM) |
| Polyethyleneglycol (3.3 kD) | 10 g/l |
| 300–310 mOs | |

The supernatant is drawn off and the pellet is incubated for 30 min at 37° C. in either Dex-saline or PBS-GA (pre-warmed to 37° C.) and centrifuged. This step is repeated with Dex-saline (or PBS-GA) at R.T.

To determine hemoglobin recovery, a sample is centrifuged for 2 minutes at 9000 rpm. in an Eppendorf centrifuge. The pellet and supernatant are separated and 180 μl of d.i. water is added to the pellets, which are lysed by rigorously vortexing. To each sample is added 1 ml Drabkins reagent, and after standing at R.T. for 15 minutes, the absorbances at 540 nm are taken. Recovery = $A_{540}$ pellet/ $A_{540}$ pellet + $A_{540}$ supernatant. The stability of the cells can be measured by incubating a sample at 100-200-fold dilution in PBS-GA, autologous plasma or whole blood for 30-60 minutes at 37° C. Hemoglobin recovery is determined by the spectrophotometric method described above or by radiolabelling of the cells. On average 70-80% of the cells survive this treatment after one hour.

The measured net hemoglobin recovery levels are on average 22-23%±2.6%.

The ATP levels in the reconstituted cells were assayed using a Sigma ATP diagnostic kit, Procedure No. 366, for quantitative, enzymatic determination of ATP in blood at 340 nm. The assay was conducted on three different reconstituted human blood samples with one measurement taken before incubation with the GIS buffer and a second measurement taken after incubation with the GIS buffer.

|  | Before GIS Incubation | After GIS Incubation |
|---|---|---|
| Sample No. 1 | 0.55 μmol/g | 2.23 μmol/g |
| Sample No. 2 | 1.68 μmol/g | 4.48 μmol/g |
| Sample No. 3 | 0.65 μmol/g | 2.54 μmol/g |

The preceding data shows that incubation in the GIS buffer increases the ATP levels by around 3- to 4-fold. The assay method was followed as per the instructions in the kit, modified for use of 1 ml samples rather than 3 ml samples.

The following cell indices were also measured on blood samples before and after the GIS incubation: MCV (mean corpuscular volume); MCH (mean corpuscular hemoglobin); and MCHC (mean corpuscular hemoglobin content).

|  | Before lyophilization | After lyophilization |
|---|---|---|
| MCV = $\frac{Hct \times 10}{cell\ count\ (mm^3)}$ | | |
| Sample A | 79.0 fl | 61.3 fl |
| B | 81.8 | 66.7 |
| C | — | 64 |
| D | — | 73.2 |
| E | 81.5 | 68 |
| F | 92.7 | 82 |
| Literative values of non-lyophilized human | | (80-96) |
| MCH = $\frac{Hgb(g/dl) \times 10}{cell\ count}$ | | |
| Sample A | 28 pg | 13.8 pg |
| B | 16.9 | 12.3 |
| C | — | 13.8 |
| D | — | 16.7 |
| E | 26.9 | 13.5 |
| F | 29.1 | 16.9 |
| Literative values of non-lyophilized human | | (27-31) |
| MCHC = $\frac{Hgb \times 100}{Hct}$ | | |
| Sample A | 34.0% | 22.6% |
| B | 20.6 | 18.4 |
| C | — | 21.5 |
| D | — | 22.9 |
| E | 33.0 | 20.0 |
| F | 31.4 | 20.6 |
| Literative values of non-lyophilized human | | (32-36) |

EXAMPLE 2

Fresh human blood was lyophilized and promptly reconstituted following the procedure described in Example 1. Before lyophilization several key glycolytic enzymes critical to normal red blood cell functioning were assayed for activity by conventional procedures. The reconstituted cells were assayed for activity of those same enzymes. The results are shown below.

|  | LYOPHILIZATION (units = IU/g Hb) | |
|---|---|---|
|  | Before | After |
| Hexokinase | 1.20 ± 0.12 | 0.68 |
| Phosphoglucose Isomerase | 48.3 ± 5.0 | 32 |
| Phosphofructokinase | 9.7 ± 2.2 | 19.5 |
| Aldolase | 2.39 ± 0.34 | 1.97 |
| Triose Phosphate Isomerase | 2903 ± 777 | 2367 |
| Glyceraldehyde 3-Phosphate Dehydrogenase | 244 ± 72 | 252 |
| Diphosphoglyceratemutase | 8.43 ± 2.23 | 3.94 |
| Phosphoglycerate Kinase | 349 ± 47.7 | 276 |
| Phosphoglyceromutase | 17.3 ± 6.7 | 20.9 |
| Enolase | 4.96 ± 0.89 | 3.43 |
| Pyruvate Kinase | 15 ± 2.14 | 13.6 |
| Lactate Dehydrogenase | 141 ± 56.4 | 146 |

These results indicate that sufficient levels of blood enzymes are present in the reconstituted cells for cell-functioning.

EXAMPLE 3

Samples of dried red blood cells were examined in the presence and absence of the cryoprotectant formulation. This formulation consisted of the following:
2.00 mM potassium chloride
1.47 mM potassium phosphate
91.89 mM sodium chloride
8.10 mM sodium phosphate
1.60 M glucose
16.00% (w/v) Polyvinylpyrrolidone (40 K MW avg.)

The cells were frozen at −80 Celsius at a 30% Hematocrit in the appropriate buffer and placed on a lyophilizer for 72 hours. The samples slowly equilibrated to room temperature during this period.

The solid material was removed and placed in a 10 mm diameter NMR sample tube. Samples were examined using a 162 MHz NMR spectrometer with cross polarization. Samples were examined using a phosphorous-31 probe.

Figure 2:
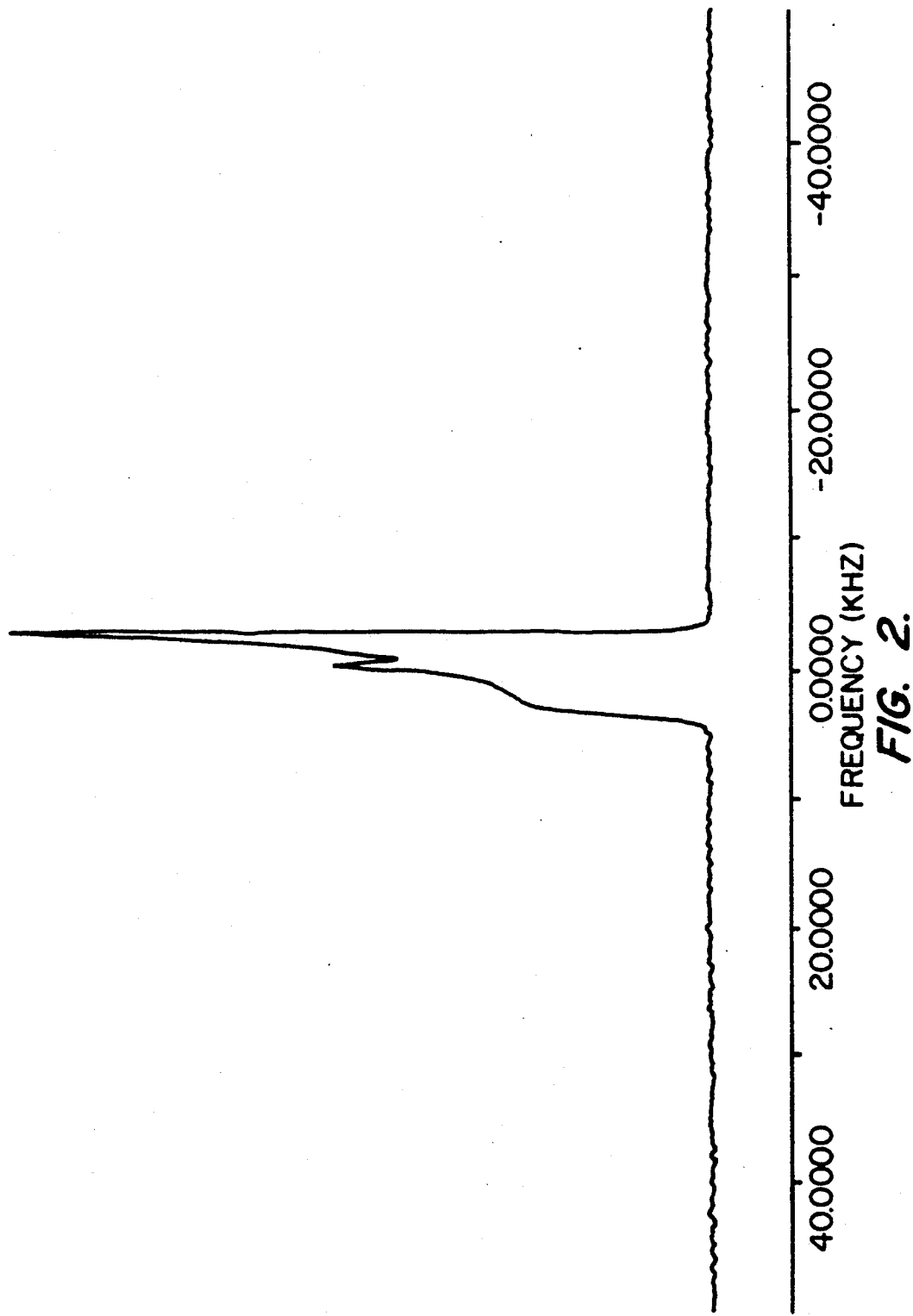
FIG. 2 is a phosphorous-31 NMR spectrum of hydrated dimyristoyl phosphatidylcholine multilamellar vesicles.

A rigid phosphate will normally produce a spectrum as depicted in FIG. 1 for solid barium diethylphosphate. The shape is indicative of a rigid phosphate group with no axial motion. The linewidth is equal to 188 ppm. Normal liquid-crystalline phospholipids provide a lineshape which is dramatically altered. This is depicted in FIG. 2 for hydrated dimyristoyl phosphatidylcholine (DMPC) multilamellar vesicles. Headgroup motion is indicated with a reduction in width to 60–80 ppm.

Figure 3:
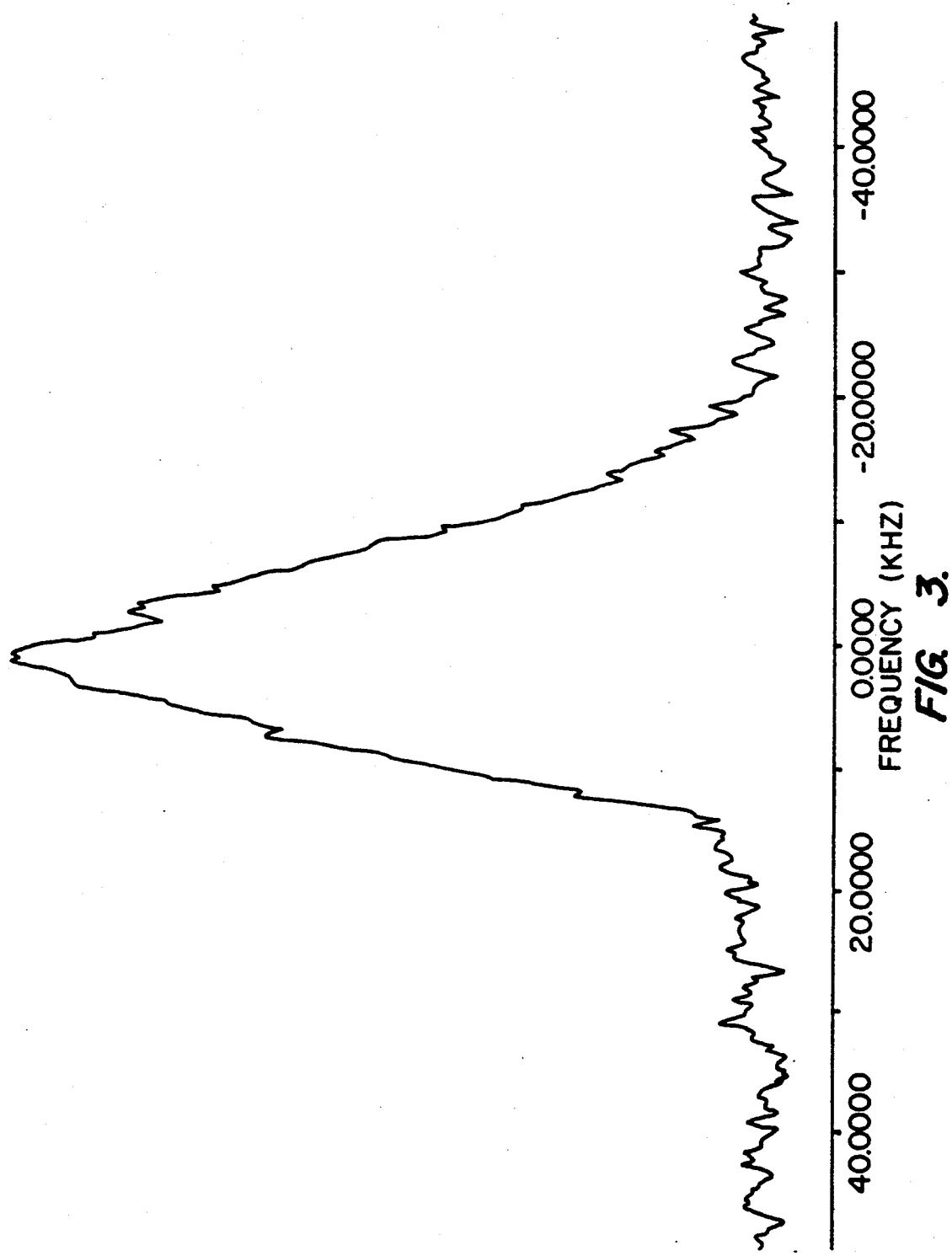
FIG. 3 is a phosphorous-31 NMR spectrum of freeze-dried red blood cells without the cryoprotectant of the invention.
Figure 4:
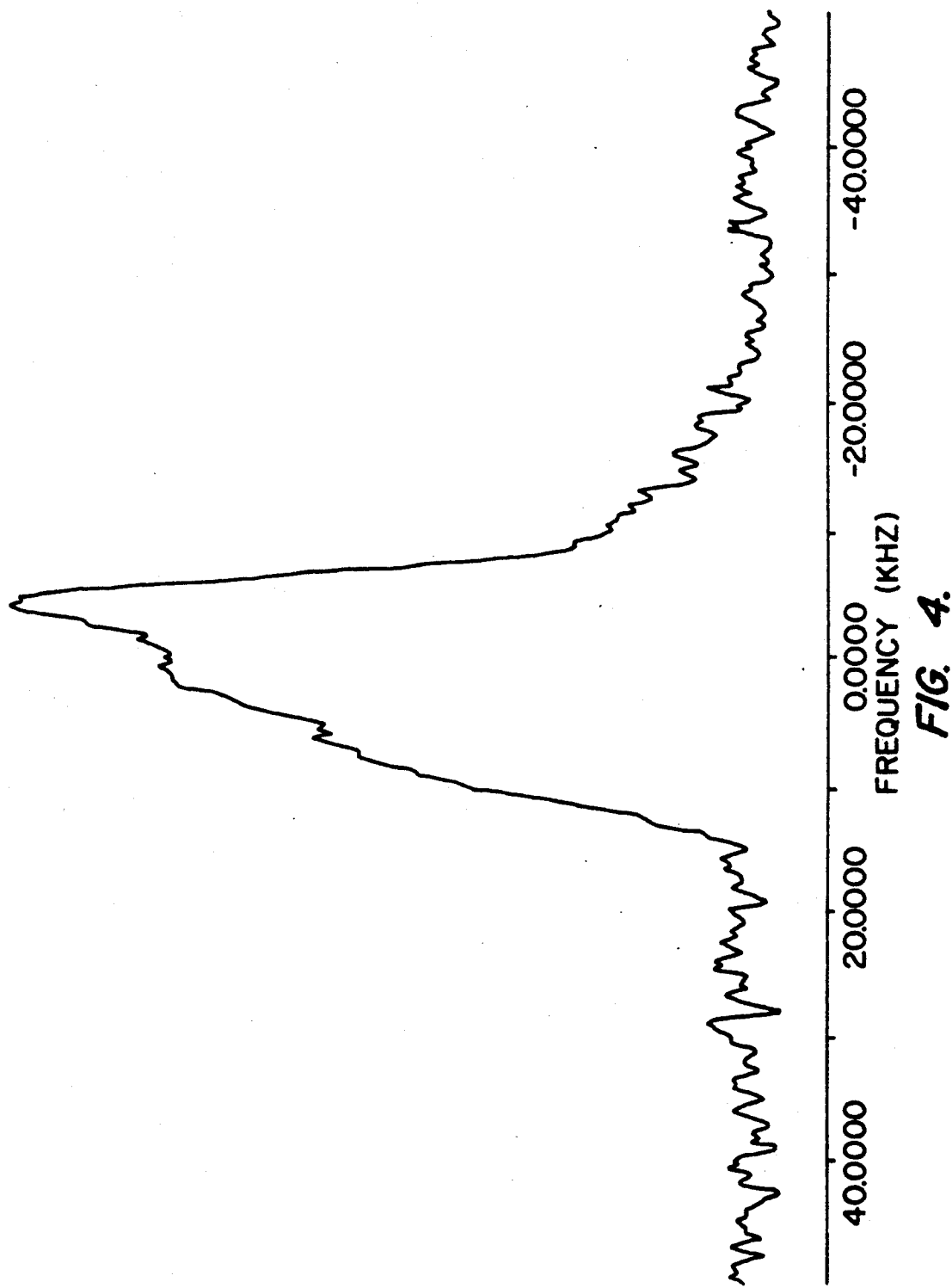
FIG. 4 is a phosphorous-31 NMR spectrum of freeze-dried red blood cells treated with the cryoprotectant formulation according to Example 3.

The spectrum for freeze-dried red blood cells without any protectant is depicted in FIG. 3. The shape is indicative of the loss of some bilayer structure and possible formation of hexagonal phase lipid structure (indicated by the maximum peak at about 2 KHz). The linewidth (105 ppm) indicates that the headgroup is rigid. The pattern is quite distinct for red blood cells dried with the protectants according to the invention, depicted in FIG. 4, which is characteristic of lipid in a semi-gel state. Note that the 2 KHz peak in FIG. 4 is reduced to a shoulder, indicating absence of or at least reduction of hexagonal phase lipid structure. The linewidth is reduced to 95.5 ppm indicating some mobility or that stereochemical alteration in the headgroup has occurred.

| Material | Linewidth | Lineshape Pattern |
| --- | --- | --- |
| Barium Diethylphosphate | 188 ppm | Rigid headgroup |
| Hydrated DMPC | 10–20 ppm (FIG. 2.) | Liquid-crystalline bilayer High mobility |
| Hydrated Dipalmitoyl Phosphatidylocholine | 60–80 ppm | Gel phase bilayer Reduced mobility |
| F/D Red Cells-Protectant | 105 ppm (FIG. 3) | Loss of bilayer structure Reduced mobility |
| F/D Red Cells | 95.5 ppm (FIG. 4) | Gel phase bilayer Intermediate mobility |

The results indicate that cells dried in the presence of the protectant solution maintain the characteristics of membrane structure associated with hydrated cells in a gel phase. The cells dried without the protectant show evidence of the loss of some bilayer structure and possible formation of hexagonal phase lipid structure which is incompatible with viability. These cells also generate a pattern characteristic of severely restricted phospholipid headgroup motion.

From the foregoing description, one skilled in the art can readily ascertain that essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A transfusably-useful erythrocyte-containing and/or hemosome-containing composition reconstituted after lyophilization characterized by a $P_{50}$ in the range of about 26–28, an oxyhemoglobin content greater than about 90% of that of normal red blood cells, morphology, and normal ATP metabolism.

2. A composition according to claim 1 comprising erythrocytes having discocytic or stomatocytic morphology.

3. A composition according to claim 2 further comprising an additive comprising a polymer or mixture of polymers having a molecular weight of from about 1 K to about 360 K in a concentration of about 12 to 30% by weight.

4. A composition according to claim 3 wherein said polymers are amphipathic.

5. A composition according to claim 3 wherein said polymers have molecular weights in the range of about 2.5 K to 360 K.

6. A composition according to claim 3, 4 or 5 wherein said polymer is selected from the group consisting of polyvinylpyrrolidone, hydroxyethyl starch and dextran.

7. A composition according to claim 6 wherein said polymer comprises polyvinylpyrrolidone of average molecular weight of 40 K.

8. A composition according to claim 7 wherein said polyvinylpyrrolidone is present in said solution in a final concentration of about 14.4% by weight.

9. A composition according to claim 8 wherein said solution further comprises a monosaccharide in a final concentration of about 7.0 to 37.5% by weight.

10. A composition according to claim 2 wherein said composition further comprises a polyanion selected from the group consisting of inositol hexaphosphate, adenosine triphosphate, pyrophosphate and tripolyphosphate.

11. A composition according to claim 10 wherein said polyanion comprises inositol hexaphosphate.

12. A composition according to claim 2 further comprising polyethylene glycol of a molecular weight in a range of about 3 to 5 KD.

13. A lyophilized erythrocyte-containing and/or hemosome-containing composition characterized by a phosphorous-31 NMR lineshape characteristic of a bilayer in a gel phase.

14. A composition according to claim 13 comprising erythrocytes.

15. A composition according to claim 14 further comprising an additive comprising a polymer or mixture of polymers having a molecular weight of from about 1 K to about 360 K in a concentration of about 12 to 30% by weight.

16. A composition according to claim 15 wherein said polymers are amphipathic.

17. A composition according to claim 15 wherein said polymers have molecular weights in the range of about 2.5 K to 360 K.

18. A composition according to claim 15, 16 or 17 wherein said polymer is selected from the group consisting of polyvinylpyrrolidone, hydroxyethyl starch and dextran.

19. A composition according to claim 18 wherein said polymer comprises polyvinylpyrrolidone of average molecular weight of 40 K.

20. A composition according to claim 14 wherein said solution further comprises a monosaccharide.

21. A composition according to claim 15, 16 or 17 further characterized by a phosphorous-31 NMR spectrum linewidth reduced by at least 8% as compared to the linewidth of a corresponding erythrocyte-containing composition lyophilized without said additive.

* * * * *

UNITED STATES PATENT AND TRADEMARK OFFICE
CERTIFICATE OF CORRECTION

PATENT NO. : 5,178,884
DATED : January 12, 1993
INVENTOR(S) : Raymond P. Goodrich, et al It is certified that error appears in the above-indentified patent and that said Letters Patent is hereby corrected as shown below:

Column 10, Line 23, "5.0" should be --6.0--

Column 11, Line 17, after "curred." add paragraph --The results may be summarized as follows:--

Column 11, Line 22, under "Linewidth 188 ppm" add --(FIG. 1)--

Column 12, Line 19, "8" should be --2--

Signed and Sealed this

Eighth Day of February, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,178,884
DATED : January 12, 1993
INVENTOR(S) : Raymond P. Goodrich et al It is certified that error appears in the above-indentified patent and that said Letters Patent is hereby corrected as shown below:

On the title page, "...which is a continuation-in-part of Ser. No. 237,583, August 25, 1988, abandoned." should be --and a continuation-in-part of Ser. No. 237,583, August 25, 1988, abandoned.--

Signed and Sealed this

Twelfth Day of July, 1994

Attest:

BRUCE LEHMAN

*Attesting Officer*    *Commissioner of Patents and Trademarks*